United States Patent [19]
Heller et al.

[11] Patent Number: 5,356,786
[45] Date of Patent: * Oct. 18, 1994

[54] INTERFERANT ELIMINATING BIOSENSOR

[75] Inventors: Adam Heller; Ruben Maidan, both of Austin, Tex.

[73] Assignee: E. Heller & Company, Austin, Tex.

[*] Notice: The portion of the term of this patent subsequent to Nov. 16, 2010 has been disclaimed.

[21] Appl. No.: 161,682

[22] Filed: Dec. 2, 1993

Related U.S. Application Data

[63] Continuation of Ser. No. 664,054, Mar. 4, 1991, abandoned.

[51] Int. Cl.$^5$ ............... C12Q 1/54; C12Q 1/28; C07C 1/00; C12M 1/40
[52] U.S. Cl. .................................. 435/14; 435/28; 435/26; 435/24; 435/288; 435/291; 435/817; 204/403; 204/157.15; 204/153.1; 429/111; 429/40; 373/80
[58] Field of Search ............... 435/14, 28, 26, 24, 435/288, 291, 817; 204/403, 157.15, 153.1; 429/111, 40; 373/80

[56] References Cited

U.S. PATENT DOCUMENTS

| | | | |
|---|---|---|---|
| 4,098,574 | 7/1978 | Dappen | 435/14 |
| 4,168,205 | 9/1979 | Danninger et al. | 435/10 |
| 4,247,297 | 1/1981 | Berti et al. | 435/24 |
| 4,356,074 | 10/1982 | Johnson | 435/190 |
| 4,375,399 | 3/1983 | Hauas et al. | 435/25 |
| 4,390,621 | 1/1983 | Bauer | 435/14 |
| 4,418,148 | 11/1983 | Oberhardt | 435/14 |
| 4,427,770 | 1/1984 | Chen et al. | 435/14 |
| 4,711,245 | 12/1987 | Higgins et al. | 204/415 |
| 4,758,323 | 7/1988 | Davis et al. | 435/26 |
| 4,776,944 | 11/1988 | Janata et al. | 204/415 |
| 4,795,707 | 1/1989 | Niiyama et al. | 435/174 |
| 4,919,767 | 8/1988 | Vadgama et al. | 435/4 |
| 4,927,516 | 5/1990 | Yamaguchi et al. | 435/817 |
| 4,938,860 | 7/1990 | Wogoman | 435/817 |
| 5,082,786 | 1/1992 | Nakamoto | 435/14 |
| 5,262,305 | 11/1993 | Heller et al. | 435/28 |

OTHER PUBLICATIONS

Nagy et al., "A New Type of Enzyme Electrode: The Ascorbic Acid Eliminator Electrode", *Life Sciences*, vol. 31, pp. 2611–2616, Pergamon Press, 1982.

Heller, A., "Electrical Wiring of Redox Enzymes", Reprinted from Accounts of Chemical Research, vol. 23, No. 5, 1990 (pp. 128–134).

Japanese Patent No. 03028752 A2 to Omochi et al., "Method for Manufacture of an Electrode Containing Immobilized Enzyme and Interfering-Substance-Eliminating Membrane," (Abstract) *Chemical Abstracts*, 114(21):203143u.

German Patent No. 3934299 C1, "Enzyme Electrodes Containing Oxidase and Peroxidase" to Schmid et al., (Abstract) *Chemical Abstracts*, 114(23):225208w.

Japanese Patent Application No. 02310457 A2, "Enzyme Biosensor For Micro Analysis of Body Fluid" (Abstract), *Chemical Abstracts*, 114(21):203111a.

*Primary Examiner*—Michael G. Wityshyn
*Assistant Examiner*—Louise N. Leary
*Attorney, Agent, or Firm*—Pravel, Hewitt, Kimball & Krieger

[57] ABSTRACT

Interferant eliminating analyte sensors and sensing process prevent erroneous assays. Glucose electrodes were coated with an oxidizing enzyme (peroxidase) which allows hydrogen peroxide to selectively oxidize ascorbate, urate, bilirubin, and acetaminophenol in the presence of glucose. Hydrogen peroxide may be added to the assayed solution or generated in situ. The oxidizing enzyme was prevented from causing undesired reduction currents at the glucose electrode by preventing contact of the oxidizing enzyme with the glucose electrode, or by increasing the applied voltage.

15 Claims, 2 Drawing Sheets

INTERFERANT ELIMINATING BIOSENSOR

This is a continuation of co-pending application Ser. No. 07/664,054 filed Mar. 4, 1991, now abandoned.

BACKGROUND OF THE INVENTION

1.) Field of the Invention

This invention relates to an improved sensor and sensing system for assaying the concentration of an analyte in a solution. More particularly, the sensor and sensing system eliminate interferants by selectively oxidizing the interferants before such interferants interfere substantially with the assay.

2.) Description of the Prior Art

Glucose is typically assayed by detecting the concentration of glucose at enzyme electrodes using glucose oxidase. Because of overlapping oxidation potentials, existing enzyme electrode sensors cannot discriminate between glucose and other electrooxidizable species (hereafter "interferants") such as ascorbate, urate, bilirubin, cysteine, and acetaminophenol. Consequently, these interfering species, and other species which also have overlapping oxidation potentials, prevent the accurate analysis of glucose levels in blood samples.

Persons skilled in the art have searched for ways to prevent the interferants from affecting the accurate analysis of glucose in blood solutions. U.S. Pat. No. 4,098,574 to Dappen appears to disclose that interferants of fluoride ion with glucose analysis performed in integral multilayer elements can be reduced or eliminated by buffering the reagent composition contained therein to a pH between 4.5 and 6.0. U.S. Pat. No. 4,247,297 to Berti et al. appears to claim a test system "highly resistant to interfering reducing substances" through the use of a test means comprising a hydrazone and 8-amino-1-naphthol-5,7-disulfonic acid.

Persons skilled in the art have also attempted to design highly specific sensors, partly in an effort to reduce the effect of interferants. U.S. Pat. No. 4,776,944 to Janata et al. appears to disclose a chemical selective sensor system which utilizes admittance modulation to detect the presence of chemicals in a fluid. Commercial variations of the glucose sensors have also utilized filtering membranes and electrostatic repulsion membranes to inhibit interferants from reaching the analyte sensing layer.

Despite the above described improvements, persons skilled in the art have not yet adequately solved the inaccuracy problems caused by interferants.

SUMMARY OF THE INVENTION

A general object of this invention is to provide improved sensors and sensing methods wherein the effect of interferants is minimized or eliminated by oxidizing the interferants before they affect the accuracy of the assay. The problems in the prior art are solved by a novel sensor for detecting analyte concentration in the solution, comprising a sensing element with a sensing surface, and wherein the sensing surface is substantially surrounded or covered by a catalyst containing layer capable of oxidizing a plurality of interferants in the presence of an oxidant. In the examples, peroxidase was the catalyst and hydrogen peroxide was the oxidant. The sensing element comprises an electrode and an analyte sensing layer in electrical contact with the electrode. The analyte sensing layer comprises an enzyme which comprises an oxidoreductase. Examples of suitable oxidoreductases include glucose oxidase for glucose analysis, lactate oxidase for lactic acid analysis, etc.

One form of the sensor comprises the electrode described above, further comprising a catalyst containing layer immobilized on top of the first layer. The catalyst containing layer operates in the presence of an oxidant to oxidize the interferant compounds prior to those compounds reaching the sensing element. In this manner the sensing element is protected from the interfering influence of the interferants.

Since the catalyst containing layer may itself negatively affect the assay, it is advantageous to prevent the catalyst containing layer from interfering with the sensing element. One method to prevent this interference entails adjusting the operating conditions such that the catalyst containing layer will no longer interfere. Alternately, a thin barrier layer between the analyte sensing layer and the catalyst containing layer may inhibit the catalyst containing layer from permeating the analyte sensing layer and thus inhibiting the catalyst containing layer from coming into contact with the analyte sensing elements. Still further, the analyte sensing layer may be crosslinked to make it less permeable to the catalyst containing layer, thus inhibiting the catalyst containing layer from coming into contact with the analyte sensing elements.

Since the oxidant itself may be undesirable in some circumstances, a methodology describing in situ production of the oxidant is provided. In this manner, the oxidant may be produced by a separate enzyme in a separate layer, or by the same enzyme used in the analyte sensing layer. The oxidant producing enzyme may be mixed with the analyte sensing layer, with the catalyst containing layer, or may itself be a separate layer.

Figure 5A:
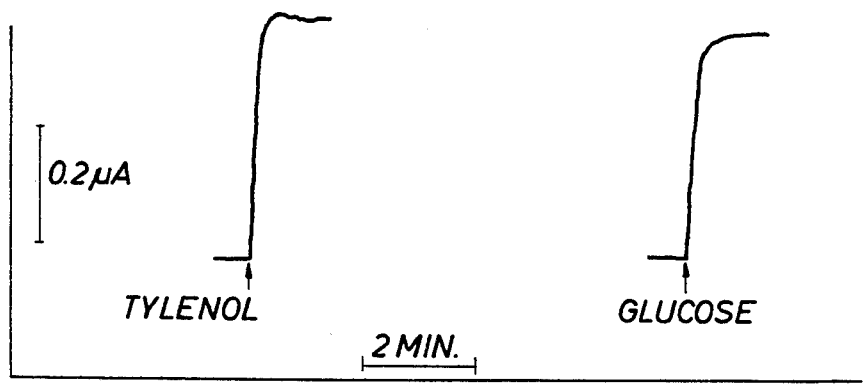
FIG. 5A shows the results of a measurement performed with an electrode of the type described in Example 1. The signals (current as a function of time) obtained upon additions of Tylenol (acetaminophen, 0.1 mM) and glucose (2 mM) are shown in the absence of hydrogen peroxide.
Figure 5B:
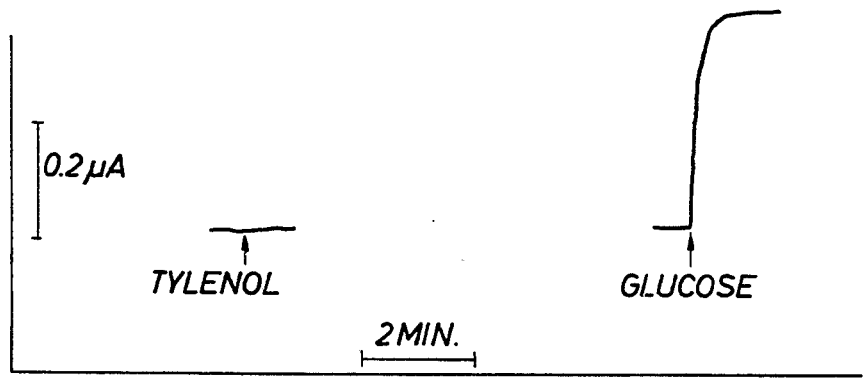

FIG. 5B shows the results of a measurement performed with an electrode of the type described in Example 1. The signals (current as a function of time) obtained upon additions of Tylenol (acetaminophen, 0.1 mM) and glucose (2 mM) are shown with hydrogen peroxide (0.1 mM) added.

Figure 6:
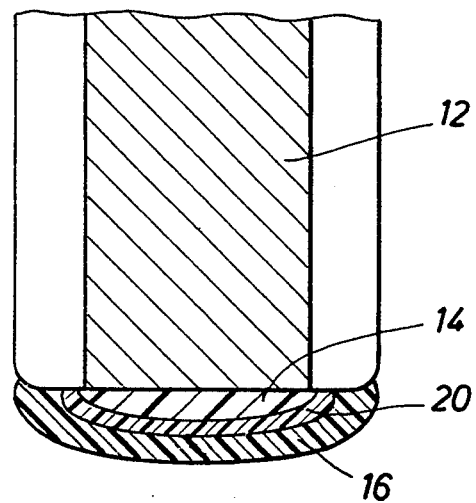

FIG. 6 is a schematic diagram of a multilayer electrode with an osmium based glucose sensing layer, and a barrier layer between the catalyst containing layer (interferant eliminating layer—i.e. immobilized peroxidase) and the analyte (glucose) sensing layer.

DESCRIPTION OF THE PREFERRED EMBODIMENTS

The device is an electrochemical analyte sensor composed of two or more layers of catalysts and electron relays (or mediators) covering a solid electrode material. In the context of this application "analyte" simply means a substance being analyzed, detected, or measured in some manner (in the Examples, glucose is the analyte). Similarly, an "interferant" is a substance that interferes in some manner with any desired analyzation, detection, or measurement process.

The preferred electrode material is glassy carbon but it may be any other electrode material such as graphite, platinum, palladium, tin oxide, conducting organic salts, etc.. Typically, a wire electrically contacts with the electrode material. Various layers of material are coated on the exposed surface of the electrode material. In some instances the electrode material itself is able to sense and detect the analyte but in most cases a special sensing layer or a chemical modification has to be applied to the electrode material.

Figure 1:
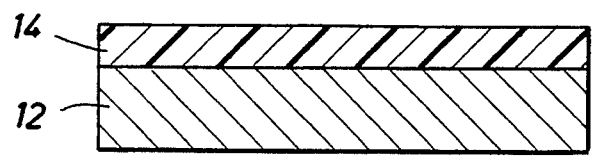
FIG. 1 is a schematic view of an electrochemical glucose biosensor having a analyte (glucose) sensing layer on top of the electrode surface (layer I).

The analyte sensing layer (layer I in FIGS. 1, 2 or 3) contains the sensing elements for the particular analyte and is in close contact with the electrode material. For the purposes of this application it is intended that the phrase "analyte sensing layer" be interpreted broadly to include the necessary sensing elements to detect and send a signal useful for analyzing the analyte. Usually this layer contains an enzyme that is in electrical contact with the electrode through electron relays incorporated in the layer or through diffusing redox mediators. Alternatively, instead of free enzymes this layer may include cells or tissues which contain enzymes. Any known methodology may be used to bring the analyte sensing layer into electrochemical contact with the electrode. One such method is described in U.S. Pat. No. 4,758,232 to Davis et al.

Suitable analyte sensing layer enzymes are oxidoreductases such as dehydrogenases or oxidases. Examples of suitable enzymes are glucose oxidase for glucose analysis, lactate oxidase for lactic acid analysis, xanthine oxidase for xanthine analysis, cholesterol oxidase for cholesterol analysis, pyruvate oxidase for pyruvic acid analysis, L-amino acid oxidases for L-amino acid analysis, D-amino acid oxidases for D-amino acid analysis, alcohol oxidase for alcohol analysis, urease for urea analysis, glycollate oxidase for glycollate analysis, sarcosine oxidase for sarcosine analysis, and other similar enzymes. In the detailed description of the preferred embodiment, glucose oxidase (GOD) is used for the analysis of glucose.

Suitable mediators are electrochemically active compounds such as metal ions, conducting organic salts, quinones and their derivatives, organometallic complexes such as ferrocenes and their derivatives, or polypyridine complexes of transition metals and their derivatives. The same type of compounds that will attach to an enzyme shell and make it electrically conductive will behave as electron relays. In the detailed description of the preferred embodiment a redox polymer based on a poly(vinylpyridine) complex of Osmium bis(bipyridine)chloride is the electron relay. This polymer is brought into close contact with the enzyme and the electrode surface using a crosslinking agent, poly-(ethylene glycol) diglycidyl ether and forming an epoxy redox gel.

The catalyst containing layer of the device contains the interferant eliminating elements. The basic component of this layer is a catalyst capable of mediating the following reaction:

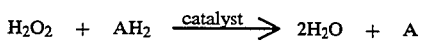

$$H_2O_2 + AH_2 \xrightarrow{\text{catalyst}} 2H_2O + A$$

In this general reaction $AH_2$, the hydrogen donor, is an interfering compound and is oxidized by hydrogen peroxide to "A"—that is, to a noninterfering compound that is no longer substantially electrochemically active. After oxidation the noninterfering compound "A" may diffuse to the analyte sensing layer but does not interfere with the analysis process because compound "A" is no longer electrochemically active. The catalyst may be a natural enzyme of the peroxidase type such as horseradish peroxidase or a synthetic or semisynthetic catalyst such as some model compound for peroxidase (for example, Iron (III) porphyrins). In the detailed description of the preferred embodiment horseradish peroxidase (POD) is used as the catalyst.

POD is an enzyme that works well as a catalyst for the above equation. The POD enzyme has a low specificity for the hydrogen donor ($AH_2$). A large number of compounds including phenols, aminophenols, diamines, indophenols, leucodyes, ascorbate and amino acids are active as such. More importantly, interferants present in physiological fluids such as ascorbate, urate, acetaminophen, bilirubin, or cysteine are rapidly oxidized by hydrogen peroxide in the presence of POD. Thus a POD containing layer will eliminate these compounds from the electrode vicinity when exposed to $H_2O_2$. It is anticipated that any other interfering compound oxidized by hydrogen peroxide in the presence of a suitable catalyst will be promptly removed using this catalyst.

Figure 2:
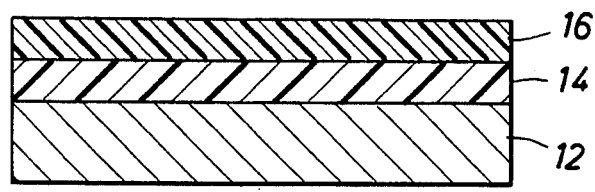
FIG. 2 is a schematic view of an electrochemical glucose biosensor with a catalyst containing layer that eliminates the interferants. This device has a peroxidase catalyst containing layer covering the glucose sensing element (layer II).

Optimally, the catalyst should cover the analyte sensing layer in such a way that the interferants will come in contact with the catalyst before reaching the analyte sensing layer (see FIG. 2). The catalyst may be positioned to cover the analyte sensing layer in this manner using two methods:

(1) using a soluble catalyst contained near the first layer by a dialysis membrane, or
(2) using an insolubilized catalyst that coats the analyte sensing layer.

In method (2), the catalyst may be attached to an insoluble matrix or it may be crosslinked with a crosslinking agent forming a gel-like structure that is no longer soluble. In the case of the peroxidase type enzymes, protein crosslinking agents such as bifunctional or polyfunctional reagents may be used. Bifunctional reagents are used to insolubilize enzymes by intermolecular crosslinking. Crosslinking agents suitable for immobilizing enzymes include glutaraldehyde, cyanogen bromide, periodate, or cyanuric chloride. In the detailed description of the preferred embodiment, horseradish peroxidase (POD) is crosslinked by two alternative methods:

(1) using glutaraldehyde as a crosslinking agent, or
(2) oxidation of the oligosaccharide groups in the POD glycoenzyme with $NaIO_4$, followed by coupling of the aldehydes formed to hydrazide groups in a polyacrylamide matrix to form hydrazones.

When the interfering compound reaches the catalyst containing layer (layer II) it is oxidized by hydrogen peroxide, thus preventing it from reaching the analyte sensing layer (layer I) and its subsequent electrochemical detection. Hydrogen peroxide is present in one of two ways:

(1) it may be added to the assayed solution, or
(2) it may be produced in situ by an enzyme of the oxidase class according to the following equation:

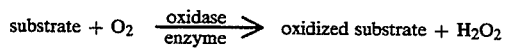

One or more enzymes capable of producing hydrogen peroxide may be included in the $H_2O_2$ generating layer as long as appropriate corresponding substrates are present in the analyzed sample. Examples of suitable enzymes are glucose oxidase with glucose as the substrate, lactate oxidase with lactic acid as the substrate, xanthine oxidase with xanthine as the substrate, pyruvate oxidase with pyruvate as the substrate, amino acid oxidase with amino acids as the substrates, choline oxidase with choline as the substrate, alcohol oxidase with alcohol as the substrate, ascorbate oxidase with ascorbate as the substrate, urate oxidase with urate as the substrate, aldehyde oxidase with aldehyde as the substrate, sarcosine oxidase with sarcosine as the substrate, etc.

The hydrogen peroxide generating enzyme may be the same enzyme that is being used in the analyte sensing layer as the analyzing enzyme. For example, in the case of a glucose sensor, part of the glucose oxidase will mediate the oxidation of glucose by the electrode through the electron relays, thus providing for the analysis of glucose. The remaining glucose oxidase will mediate the oxidation of glucose by oxygen, thus generating hydrogen peroxide that will be subsequently used in the catalyst containing layer for elimination of the interferants.

This hydrogen peroxide generating enzyme will be contained in a third layer (FIG. 3, layer III) and/or it can be mixed together with the catalyst containing layer, or in the analyte sensing layer. The hydrogen peroxide generating enzyme is preferably located near the interferant eliminating catalyst. This enzyme also may be used as a soluble enzyme contained by a membrane or as an insoluble enzyme attached to the previous layers. In the detailed description of the preferred embodiment (Example 3) lactate oxidase is used as the hydrogen peroxide generating enzyme according to the following equation:

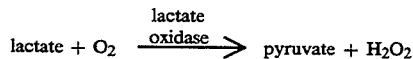

In this example lactate oxidase (LOD) is immobilized on top of the peroxidase layer using glutaraldehyde as the crosslinking reagent.

The multilayer electrodes prepared in this way may be used for all the different kinds of electrochemical sensing methods. Amperometric, potentiometric, conductimetric or impidimetric devices as well as immunoelectrodes can benefit from the use of the interferant eliminating layers. For the purpose of demonstration the electrodes are used as an amperometric sensing device.

Measurements are performed in a medium containing an electrolyte and using a three electrode configuration: the multilayer electrode is used as the working electrode, saturated calomel electrode (SCE) or Ag/AgCl is used as a reference electrode, and a metal wire is used as the counter electrode. Alternatively a two electrode configuration may be used (for instance, with Ag/AgCl as both the reference and counter electrodes).

In the detailed description of the preferred embodiment the multilayer electrode is used as the working electrode, a saturated calomel electrode (SCE) is used as the reference electrode, and a platinum wire is used as the counter electrode in a glass cell containing an electrolyte.

The cell may contain the analyzed sample or this sample may be injected into the cell at a later time. An electrochemical potential is applied to the working electrode with respect to the reference electrode and the current flowing is measured as a function of time. The choice of the electrochemical potential is dependent upon the mediator or electron relay used, as well as the enzyme properties.

The measured current is generally proportional to the concentration of the species being oxidized. When the (interferant eliminating) catalyst containing layer is not active, both the analyte and the interfering species are being oxidized. Thus the measured current is proportional to both concentrations and the reading is a false reading. When the catalyst containing layer is active, the interferants are enzymatically oxidized in the catalyst containing layer and do not reach the analyte sensing layer. In the latter case the current being measured is proportional only to the analyte concentration.

Under certain operating conditions the peroxidase enzyme (or the alternative catalyst) may mediate the electrochemical reduction of hydrogen peroxide. This electrochemical reaction is also mediated by the same electron relays that are used in the analyte sensing element (layer I). This process will result in a reduction current superimposed on the oxidation current of the analyte and the net current will no longer be proportional to the analyte concentration. This is an undesired situation and it may be prevented in one of the two methods:

(1) by making the potential of the working electrode more oxidative in such a way that the reduction process will no longer proceed; while the oxidations will still proceed.
(2) by preventing electrical contact between the catalyst (peroxidase) and the electron relays.

Preventing electrical contact as in method (2) above may be achieved by either:

(1) applying a thin electrically insulating barrier layer between the analyte sensing layer and the catalyst containing layer. This barrier may be cast from a variety of film or membrane forming polymers such as cellulose acetate or other cellulose derivatives, polycarbonates, or perfluorinated membranes, etc. FIG. 6 shows a schematic diagram of a multilayer electrode with an osmium based glucose sensing layer, and a barrier layer between the catalyst containing layer and the glucose sensing layer.

(2) by further crosslinking the analyte sensing layer to make it less permeable to the peroxidase enzyme. If the peroxidase catalyst is no longer able to permeate there will be no electrical contact between the electron relays and the peroxidase and no reduction current will be observed. Any protein crosslinking agent such as glutaraldehyde, cyanogen bromide, periodate, cyanuric chloride may be used to further crosslink the protein in the analyte sensing layer.

The following specific examples illustrate how the invention may be carried out but should not be considered as limiting the invention.

EXAMPLE 1

A piece of glassy carbon rod (10 mm long, 3 mm diameter, V 25 Vitreous Carbon, Atomergic Chemetals Corp., Farmington, N.Y.) was sealed in a glass tube with insulating epoxy resin (Quick Stick—GC Electronics, Rockford, Ill.). A copper wire was attached to the rear end of the rod with electrically conducting silver epoxy (Epo-tek H2OE, Epoxy Technology Inc., Billerica, Mass.). The top end of the glass tube was polished with sand paper (grit 600) until a smooth surface was obtained, exposing a 3 mm disc of glassy carbon (the electrode surface). The electrode surface was pretreated by sequentially polishing with alumina powder (5.0, 1.0 and 0.3 micrometer particle size). After each polishing step the electrode surface was rinsed with deionized water, sonicated for 3 minutes and dried under a stream of nitrogen.

Synthesis of the Osmium Redox Polymer, ("POs-EA")

Cis-bis(2,2'-bipyridine-N,N')dichloroosmium(II)[-Lay, P. A.; Sargeson, A. M.; Taube, H., *Inorg. Synth.*, Vol. 24, 1986, pp. 291–306] (0.494 g, 0.864 mmol) and poly(4-vinylpyridine) (PVP, Polysciences- Worrington, Pa., MW 50,000) (0.430 g, 4.09 milliequivilant) were heated under nitrogen at reflux in 18 mL ethylene glycol for 2 h. After cooling to room temperature, 30 mL Dimethyl formamide and 1.5 g 2-bromoethylamine hydrobromide (7.3 millimole) were added and the solution was stirred at 45° C. overnight. The crude polymer was precipitated by pouring the solution into rapidly stirred acetone. The hygroscopic precipitate was collected, dissolved in H2O, filtered, and precipitated as the PF6- salt by addition of a solution of NH4PF6. The dry PF6- salt (0.49 g) was then dissolved in 20 mL acetonitrile, diluted with 50 mL H2O and stirred over 5.2 g anion exchange beads (Bio-Rad AG1-X4, chloride form) for 2 hours. This solution was filtered, and then evaporated in vacuum to about 10 mL. Concentrated HCl was then added to make the solution pH 2, and the solution was dripped into rapidly stirred acetonitrile. The precipitate was filtered and dried in a vacuum desiccator.

Preparation of the analyte (glucose) sensing layer (layer I) comprised preparing a solution containing 2 mg/ml osmium redox polymer (POs-EA), 0.12 mg/ml polyethylene glycol diglycidyl ether (Polysciences MW 400), and 1 mg/ml glucose oxidase (Sigma type X, St. Louis, Mo., 128 units/mg) in a 5 mM HEPES buffer solution, pH 7.8. A one microliter droplet of the solution was applied on the electrode surface. The electrode was left in a vacuum desiccator at room temperature for 48 hours to set up.

The glucose sensing layer was further crosslinked by dipping the electrode in a 0.25% glutaraldehyde solution for 5 seconds, followed by rinsing with a phosphate buffer (pH 7.2, 0.1 molar ("M")) solution for 30 minutes. The purpose of this step is to avoid electrochemical contact between the electron relays and the peroxidase in the next layer.

The catalyst (POD) containing layer (layer II) was prepared by depositing 5 microliters of a POD (Sigma, type I, 85 units/mg) solution (100 mg/ml in a 0.1M phosphate buffer pH 7.2 containing 5 mg/ml glutaraldehyde) on top of the barrier layer and was left for two hours to set up.

Electrochemical measurements were performed with a Princeton Applied Research Model 273 potentiostat/-galvanostat and recorded on a x-y-t chart recorder. Measurements were performed in a cell containing 5 ml of an electrolyte solution (0.1M phosphate buffer, pH 7.2 and 0.1M NaCl) using a three electrode configuration. The multilayer electrode was used as the working electrode, a saturated calomel electrode (SCE) was used as the reference electrode, and a platinum wire was used as the counter electrode. The potential of the working electrode was held at 400 mV with respect to the SCE electrode and the current flowing was measured as a function of time. Five microliters of a stock solution of glucose or of the interferant were added to the electrolyte solution and rapidly mixed. Stock solutions of the interferant compounds (ascorbate, urate, bilirubin and acetaminophen) were prepared fresh because such compounds tend to decompose when left standing.

Figure 4A:
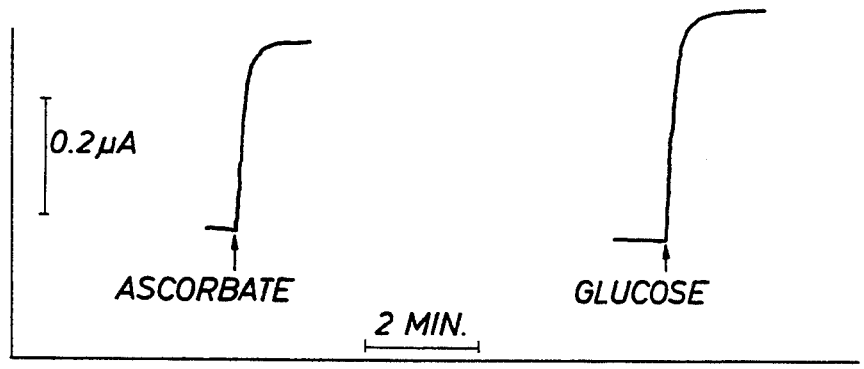
FIG. 4A shows the results of a measurement performed with an electrode of the type described in Example 1. The signals (current as a function of time) obtained upon additions of ascorbate (0.1 millimolar ("mM")) and glucose (2 mM) are shown in the absence of hydrogen peroxide.
Figure 4B:
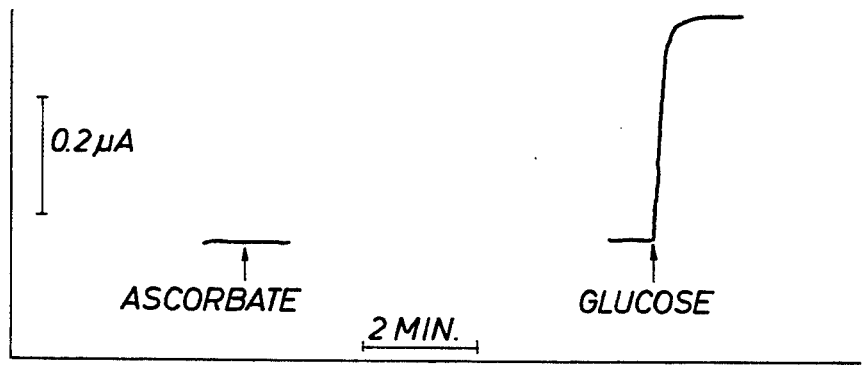
FIG. 4B shows the results of a measurement performed with an electrode of the type described in Example 1. The signals (current as a function of time) obtained upon additions of ascorbate (0.1 millimolar ("mM")) and glucose (2 mM) are shown with hydrogen peroxide (0.1 mM) added.

FIGS. 4A and 4B show the results of an experiment using a sensor as described above. In this experiment, glucose (final concentration 2.0 mM) and ascorbate (final concentration 0.1 mM) were separately added to a separate electrolyte solution and mixed rapidly. FIG. 4A shows the currents measured in the absence of hydrogen peroxide. FIG. 4B shows the currents measured in the presence of hydrogen peroxide (0.1 mM).

FIGS. 5A and 5B show the results of a similar experiment for different interferants. In this experiment, glucose (final concentration 2.0 mM) and acetaminophen (Tylenol) (final concentration 0.1 mM) were separately added to a separate electrolyte solution and mixed rapidly. FIG. 5A shows the currents in the absence of hydrogen peroxide. FIG. 5B shows the currents measured in the presence of hydrogen peroxide (0.1 mM).

As shown in FIGS. 4A, 4B, 5A, and 5B, when $H_2O_2$ is present the false signal from the interferant is substantially reduced. The glucose signal is not affected by the catalyst containing layer that eliminates the interferants. Similar results are obtained when uric acid or bilirubin are used as the interferants instead of ascorbate or Tylenol. Similar results are also obtained when a mixture of the interferants is used. It is anticipated that similar results will be obtained from other interferants (such as Cysteine) that are oxidized by hydrogen peroxide in the presence of the catalyst (peroxidase) containing layer. The results shown in FIGS. 4A, 4B, 5A, and 5B are from experiments done with separate additions of glucose and the interferant. When a mixture containing glucose and one or more of the interferants is injected in the presence of $H_2O_2$ the current measured is equivalent to the measured for the injection of glucose alone. This indicates that the interferant eliminating catalyst layer works as expected and prevents multiple interferants from reaching the electroactive layer.

It is anticipated that the procedure described in Example 1 is a preferred embodiment that will perform in a medium where hydrogen peroxide may be added to the analyte solution from an external source. Examples of applications of this method include use for clinical analysis of samples (ex vivo), or analysis of samples in industrial processes.

EXAMPLE 2

Figure 3:
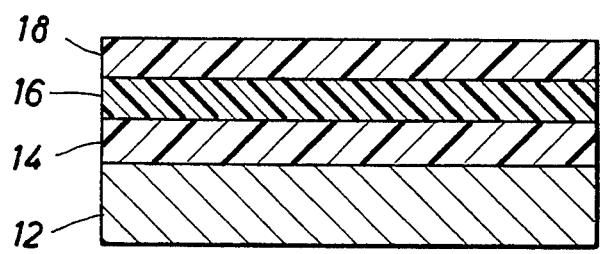
FIG. 3 is a schematic view of an electrochemical glucose biosensor with an catalyst containing layer that eliminates interferants and an oxidant (hydrogen peroxide) generating layer. This device has a layer of lactate oxidase (layer III) covering the catalyst containing layer. The purpose of layer III is to use lactic acid and oxygen to generate the hydrogen peroxide needed in the catalyst containing layer.

An electrode was prepared as described in Example 1. On top of the catalyst containing layer a hydrogen peroxide generating layer containing lactate oxidase (LOD) was immobilized by crosslinking it with glutaraldehyde (FIG. 3). This layer was prepared by depositing 5 microliters of a LOD (Finnsugar, Schaumburg, Ill., 33 units/mg) solution (100 mg/ml in a 0.1M phosphate buffer pH 7.2 containing 5 mg/ml glutaraldehyde) on the POD layer. The sensor was then left for two hours to set up.

The experimental use of this electrode was similar to that described in Example 1 with the provision that lactate replaced hydrogen peroxide as the oxidant for the interferants. Thus, hydrogen peroxide was not added to the analyte solution. The results obtained with this electrode were similar to the results described in Example 1.

It is anticipated that the procedure described in Example 2 is a preferred embodiment that will perform in a medium where it is undesirable to add hydrogen peroxide from an external source. Examples of such applications are in vivo measurements, in use as disposable sensors for analysis of small amounts of analyte solution (for example, blood drops), or for use in industrial fermenters or reactor processes.

EXAMPLE 3

An electrode was prepared as described in Example 1 for the electrode surface pretreatment and analyte sensing layer preparation. This layer was not further crosslinked with glutaraldehyde nor was it coated with a barrier layer. The catalyst containing layer was coated directly on top of the analyte sensing layer by immobilizing POD on a hydrazide polymer matrix. Specifically, the catalyst containing layer was immobilized as follows: Solution (A) comprised 5 mg/ml polyacrylamide hydrazide (Water soluble, Sigma #P9905) dissolved in water. Solution (B) comprised 2 mg Peroxidase (Sigma, type VI, 260 units/mg) dissolved in 100 microliters 0.1M sodium bicarbonate solution. Sodium periodate (50 microliters of a 12 mg/ml solution) was added to solution (B) and that solution was incubated in the dark at room temperature (20°-25° C.) for 2 hours.

After the incubation, 7.5 microliters from Solution (A) were added to Solution (B) and 10 microliters of the mixture were applied on top of the glucose sensing layer. The electrode was left to set up for 2 hours and then used.

It is understood that the above-described method using Solutions (A) and (B) are interchangeable with similar procedures using glutaraldehyde (or similar compounds), and vice versa. The method using Solutions (A) and (B) tends to be milder than other methods because it tends to destroy less of compounds it contacts.

The experimental use of this electrode was similar to that described in Example 1 with the provision that a more oxidative potential (500 mV vs. SCE instead of 400 mV vs. SCE) was applied to the working electrode.

The results obtained with this electrode were similar to the results described in Example 1.

It is anticipated that the procedure described in Example 3 is a preferred embodiment for a sensor that only needs to perform for a short time period. This sensor tends to require a more oxidative potential for its use. The higher potential employed tends to decrease the useful life of the sensing element electrode. The advantage of this procedure is that it is simpler to apply since is involves one less step that the procedure outlined in Example 1 (i.e., this procedure does not entail application of an intermediate layer between the analyte sensing layer and the catalyst containing layer).

The interferant eliminating effect of this invention as described in all three examples is enhanced by the beneficial influence on the long term stability of the sensor by protecting the electroactive layer from deactivation by oxidation products. Specifically, elimination of the urate ion tends to have a beneficial effect on the long term stability of the sensors.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein or in the steps or in the sequence of steps of the methods described herein without departing from the spirit and scope of the invention as described in the following claims. Similarly, isomers and homologs of reactants may be used and still come within the scope of the invention.

What is claimed is:

1. A biosensor comprising:
   an electrode on which an analyte is electrooxidized at a given applied potential; and
   an interferant-eliminating layer substantially covering the electrode but electrically isolated therefrom at the given applied potential,
   said interferant-eliminating layer comprising a catalyst which is capable of catalyzing substantial oxidation of a plurality of interferants but not substantial oxidation of the analyte,
   wherein the catalyst mediates the following reaction:

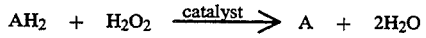

where $AH_2$ represents an interfering compound and A represents a non-interfering compound.

2. The biosensor of claim 1, wherein the catalyst is a natural or synthetic enzyme.

3. The biosensor of claim 2, wherein the enzyme is peroxidase.

4. The biosensor of claim 3, wherein the peroxidase is horseradish peroxidase, cytochrome c peroxidase, chloroperoxidase, lactoperoxidase, thyroid peroxidase, Japanese horseradish peroxidase a, Japanese horseradish peroxidase c, myeloperoxidase, NADH peroxidase, turnip peroxidase $A_1$, turnip peroxidase B, turnip peroxidase D, or glutathione peroxidase.

5. The biosensor of claim 2, wherein the catalyst is an enzyme having iron (III) porphyrins.

6. The biosensor of claim 1, wherein an insulating barrier is positioned between said catalyst and said electrode.

7. The biosensor of claim 6, wherein said insulating barrier is a membrane.

8. The biosensor of claim 7, wherein said membrane is cellulose acetate, polycarbonate, or perfluorinated membrane.

9. The biosensor of claim 1, wherein said catalyst is immobilized within a polymeric matrix.

10. The biosensor of claim 1, wherein said electrode comprises an enzyme mediating oxidation of said analyte.

11. The biosensor of claim 10, wherein said enzyme is an oxidoreductase.

12. The biosensor of claim 11, wherein said oxidoreductase is glucose oxidase, lactate oxidase, xanthene oxidase, cholesterol oxidase, pyruvate oxidase, L-amino acid oxidase, D-amino acid oxidase, alcohol oxidase, urease, urate oxidase, aldehyde oxidase, glycollate oxidase, or sarcosine oxidase.

13. The biosensor of claim 12, wherein the oxidoreductase is glucose oxidase.

14. A process for analyzing an analyte in the presence of interferants in a sample comprising the steps of:
contacting a sample with an interferant eliminating biosensor having an electrode and an interferant eliminating catalyst;
substantially oxidizing interferants in said sample by an oxidation reaction catalyzed by the interferant eliminating catalyst; and
detecting the analyte at the electrode in the absence of substantial interference.

15. The process of claim 14, wherein said catalyst mediates the following reaction:

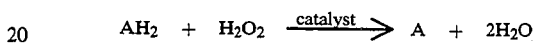

where $AH_2$ represents an interfering compound and A represents a non-interfering compound.

* * * * *